United States Patent [19]
Hunjan et al.

[11] Patent Number: 5,656,030
[45] Date of Patent: Aug. 12, 1997

[54] BIDIRECTIONAL STEERABLE CATHETER WITH DEFLECTABLE DISTAL TIP

[75] Inventors: Kulbir Singh Hunjan, Cambridge; Josef V. Koblish, Framingham; Thomas P. Coen, Westborough, all of Mass.

[73] Assignee: Boston Scientific Corporation, Natick, Mass.

[21] Appl. No.: 445,601

[22] Filed: May 22, 1995

[51] Int. Cl.$^6$ .................................................. A61M 37/00
[52] U.S. Cl. .................................................. 604/95; 604/264
[58] Field of Search ........................ 604/95, 264, 280, 604/284

[56] References Cited

U.S. PATENT DOCUMENTS

| | | | |
|---|---|---|---|
| 5,037,391 | 8/1991 | Hammerslag et al. | 604/95 |
| 5,108,368 | 4/1992 | Hammerslag et al. | 604/95 |
| 5,190,050 | 3/1993 | Nitzsche | 128/772 |
| 5,228,441 | 7/1993 | Lundquist | 128/642 |
| 5,242,441 | 9/1993 | Avitall | 606/41 |
| 5,275,151 | 1/1994 | Shockey et al. | 604/95 X |
| 5,322,064 | 6/1994 | Lundquist | 128/642 |
| 5,327,906 | 7/1994 | Fideler | 604/95 X |
| 5,330,466 | 7/1994 | Imran | 604/95 X |
| 5,364,352 | 11/1994 | Cimino et al. | 604/95 |

*Primary Examiner*—Michael Powell Buiz
*Assistant Examiner*—N. Kent Gring
*Attorney, Agent, or Firm*—Pearson & Pearson

[57] ABSTRACT

A bidirectional catheter with a deflectable tip at a distal end includes a handle at a proximal end and a tubular member extending between the tip and the handle. The handle includes a first piston member slidably mounted in a handle base with proximal ends of steering wires secured in the handle. The steering wires extend through the tubular member with respective distal ends thereof secured to circumferentially spaced portions of the distal end tip. Axial displacement of the piston member in a second direction conversely urges deflection of the distal end tip in a second direction by tensioning the other wire relative to the first wire. The piston member can include another piston member slidable in the first piston member with the proximal ends of the steering wires secured in the first mentioned piston member and the handle member, respectively, and with the other piston member supporting a proximal end of the tubular member.

24 Claims, 2 Drawing Sheets

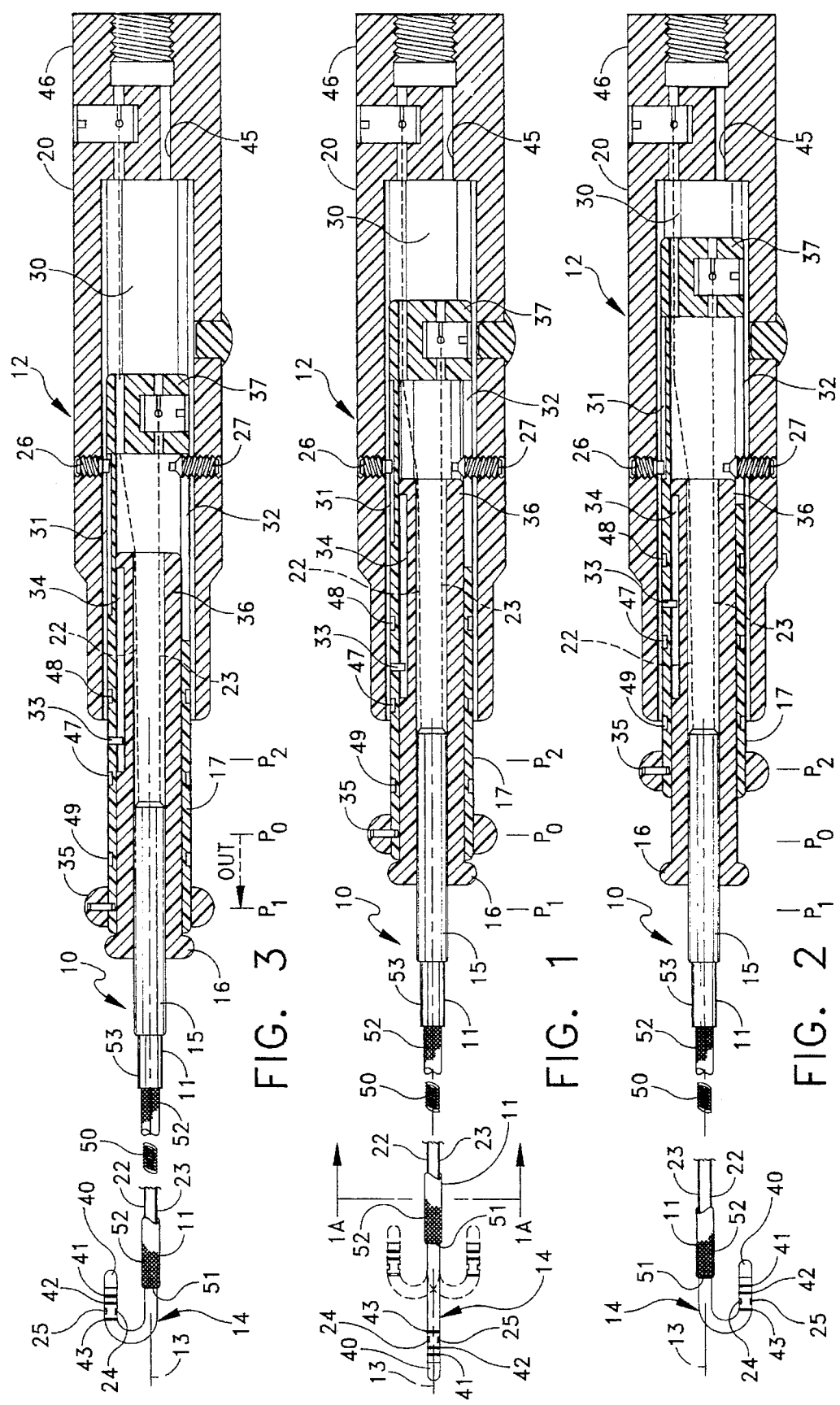

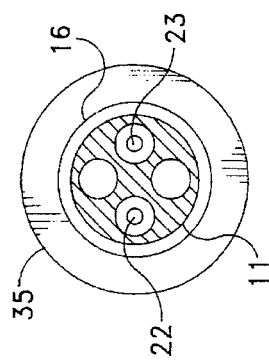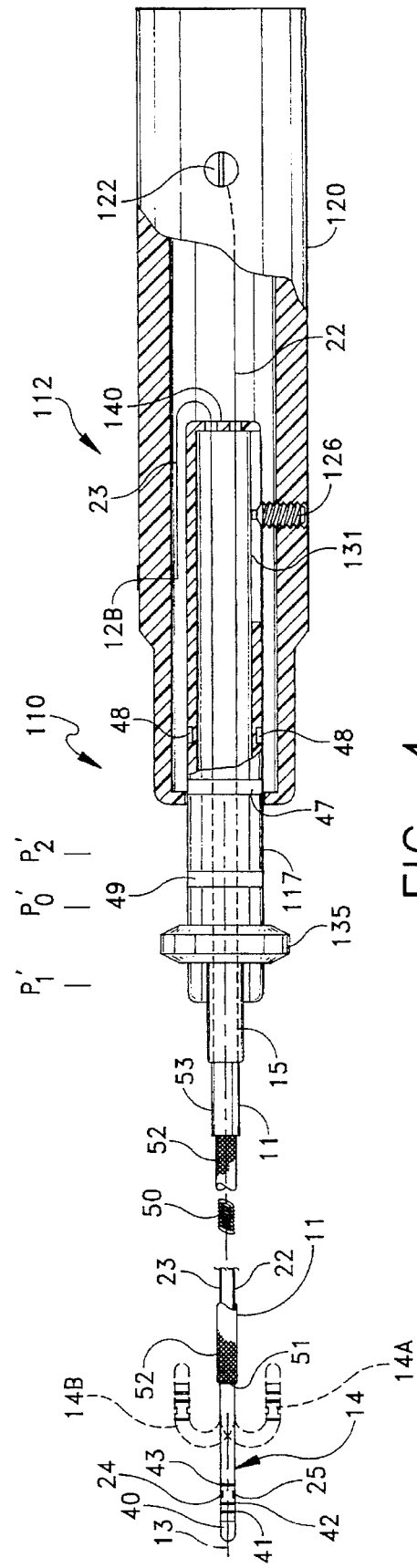

1

BIDIRECTIONAL STEERABLE CATHETER WITH DEFLECTABLE DISTAL TIP

BACKGROUND OF THE INVENTION

1. Field of the Invention

This invention relates to catheters generally and more particularly to steering mechanisms that promote the transit of such catheters through the blood vessels of a patient.

2. Description of Related Art

Steerable mechanisms have been developed to facilitate the transit of catheters through a patient's blood vessels. In practice, a surgeon typically observes the catheter fluoroscopically and maneuvers the catheter by selective rotation and deflection of a steering mechanism of the proximal end of the catheter. The rotation and deflection at the proximal end bends or deflects the tip of the catheter and enables the surgeon to steer the catheter as it advances through the tortious path often found during the transit through a patient's blood vessels.

In many applications the ability to steer the catheter is crucial to the success of the therapeutic protocol and can be a factor in reducing risk to and trauma of the patient. Moreover, the ability to steer the catheter impacts the speed and ease by which the surgeon can properly position the distal end, particularly during heart mapping protocols.

The distal ends of some steerable catheters are formed of a shape memory material or structure, such as a coil spring, so that the application of a force to a steering mechanism in the form of a steering cable deflects the distal tip from its normal position. Then as the tension in the cable is released, the distal end tends to return to its normal position. Other prior art steering mechanisms are often carried within the catheter or as part of the wall structure of the catheter to improve the response of the distal end tip to a steering force applied at the proximal end. Such steering mechanisms are designed to simplify the surgeon's task of orienting the distal end tip for deflection in a proper direction, and following United States Letters Patents and United States Patent Application describe various steering mechanisms for use with catheters:

- U.S. Pat. No. 4,798,598 (1989) Bonello et al.
- U.S. Pat. No. 5,037,391 (1991) Hammerslag et al.
- U.S. Pat. No. 5,108,368 (1992) Hammerslag et al.
- U.S. Pat. No. 5,190,050 (1993) Nitzsche
- U.S. Pat. No. 5,228,411 (1993) Lundquist
- U.S. Pat. No. 5,242,441 (1993) Avitall
- U.S. Pat. No. 5,322,064 (1994) Lundquist
- U.S. Ser. No. 08/138,863 (1993) Mirarchi et al., now U.S. Pat. No. 5,562,619.

Bonello et al. disclose a catheter having a distal end with an overcoated coil spring formed with closely spaced coils at distal and proximal end portions thereof and with relatively widely spaced coils at a central portion. A traction member connects to one side of the coils in the distal end portion and extends distally through the catheter and a proximal handle. Retraction of the traction member by a control device in the handle urges the coil spring to bend about its central portion. Upon releasing the traction member from its retracted condition, the coil spring tends to urge the distal end of the catheter to resume its normal condition.

Each of the Hammerslag et al. patents disclose a steering mechanism for use in a steerable guidewire or catheter. The steering apparatus includes a flexible post disposed in the guidewire or catheter near a flexible distal end thereof. A plurality of circumferentially spaced steering wires connects to the flexible post intermediate its distal end and its fixed proximal base and extends through the guidewire or catheter to a handle. Retracting certain steering wires relative to the others deflects the steering post and consequently urges a similar deflection of the flexible distal end of the catheter or guidewire. Another embodiment discloses a flexible steering ribbon having an intermediate hinged portion positioned in a flexible distal end of a guidewire or catheter. Two steering wires extend from a handle of the guidewire or catheter along opposed sides of the ribbon and secure to a distal end of the ribbon. Retraction of one wire relative to the other causes the ribbon to bend at the hinge and deflects the distal end of the guidewire or catheter.

Nitzsche discloses a steering mechanism comprising three elongated, thin flat shims sandwiched together at a distal end of the shims and disposed at the distal tip of the catheter. A structure within the catheter tube supports and fixes the proximal position of the center shim. A first cable connects the proximal end of one of the other two shims with a handle; a second cable elastically connects the third shim to the handle. Proximal displacement of a slide portion stretches the elastic cable while sliding the shim connected to the other cable proximally to deflect thereby the distal end of the sandwich. When the slide is released, the elastic anchor contracts and returns the sandwich to its original orientation.

Each Lundquist reference discloses a catheter that includes an elongated tube and proximal handle. Steering wires and a torque tube extend from the handle distally through the tube with distal ends of the steering wires secured to spring elements extending from the distal end of the torque tube. A proximal end of each of the steering wires secures to opposed portions of a rotatable eccentric secured in the handle. The torque tube rotates the distal end responsive to rotation of the handle, while rotation of the eccentric urges deflection of the distal end. Specifically, rotation of the eccentric in a first direction tensions one of the steering wires and reduces the tension of the other steering wire. The resulting differential tensioning of the steering wires deflects the end selectively toward the steering wire under the greater tension. Another embodiment disclosed by Lundquist in U.S. Pat. No. 5,322,064 includes first and second rotatable collars on a handle that attach to the first and second steering wires, respectively, so that selective rotation of the collars varies the relative tension of the associated steering wire to enable radial deflection an X-Y plane and, by rotation of the handle, in a transverse Z plane.

In Avitall a steering wire extends through a catheter between a sliding portion of a handle at the proximal end of the catheter and a flexible portion at a rotatable distal tip. Retracting the slide handle deflects the distal tip from its normal linearly extending axial orientation.

U.S. patent application Ser. No. 08/138,863 to Mirarchi et al. now U.S. Pat. No. 5,562,619 discloses a steerable catheter including a steering wire that extends between and connects a distal end tip with a handle at the proximal end. A proximal portion of the handle attaches to the catheter tube. Sliding a base portion of the handle relative to the proximal portion in first and second directions respectively increases and decreases the tension on the cable to enable deflection and return to an undeflected condition. In an alternative embodiment, an intermediate portion of the cable extends along a looped path defined in the base of the handle so that the handle functions as a movable pulley. Consequently a given axial displacement of the handle produces twice that displacement of the cable at the distal end.

Although the foregoing prior art references describe catheters with steering mechanisms for deflecting the distal tip, they all are characterized by restrictions that limit their convenient use. For example, the steering mechanisms disclosed by Mirarchi et al., Nitzsche and Bonello can only be deflected in a single direction and require the surgeon to rotate the handle up to 180° to orient the distal end properly for deflection in a desired direction. Since repeated reorientations of the catheter tip frequently are required, the therapeutic protocol of these devices necessitates extra work, skill and effort on the part of a surgeon and prolongs the procedure. Each of the Lundquist references provides for bidirectional bending of the distal end thereby limiting the angular displacement to 90°. However, the rotary displacement of the eccentrics or separate collars can be inconvenient to surgeons accustomed to linear actuators and may even require the surgeon to use both hands. Additionally, at least one embodiment disclosed by Lundquist requires separate controls that may lead to mistakes in steering.

The pulley arrangement disclosed by Mirarchi et al. provides the user with a slide apparatus that has a greater than unity mechanical advantage over the devices disclose by others of the references. That is, for a relatively short displacement of the slide handle relative to the catheter, the steering wire is displaced at a multiplied rate. This provides for greater ease of use of the device. Nevertheless, the apparatus disclosed by Mirarchi et al. has the previously discussed limitation of single direction deflection.

Thus, steering mechanisms of the prior art fail to provide a handle with a slide mechanism for selectively deflecting the distal end of the catheter tube in two directions relative to an axial orientation. These steering mechanisms also fail to disclose a bidirectional steerable deflectable catheter in which the steering mechanism also provides a greater than unity displacement of the distal end tip for a given displacement of a slide mechanism in at least one of the two deflectable directions.

SUMMARY

An object of this invention is to provide a catheter with an improved handle structure for deflecting a distal catheter tip in two directions.

Another object of this invention is to provide a catheter with a bidirectional deflectable distal tip that is conveniently actuated by a slide mechanism.

Another object of this invention is to provide a steerable catheter that is conveniently used by surgeons and reduces the time and skill required to orient and position a distal end tip thereof.

Still another object of this invention is to provide a bidirectional catheter in which a steering mechanism provides a greater than unity displacement of a distal end of a catheter in at least one of the deflectable radial orientations for a given displacement of a handle portion.

Yet another object of this invention is to provide a bidirectional steerable catheter with a steering mechanism that is convenient and easy.

A further object of this invention is to provide a bidirectional catheter including a proximal handle that enables a surgeon to maneuver and deflect the distal end tip of a catheter by proximal manipulation of the handle.

According to one aspect of this invention an improved bidirectional steerable catheter with a proximal handle has a radially, flexible distal end tip that is moveable from a neutral position to a first and second deflected position by steering means. The steering means includes a first and second handle portion and steering wires extending between the handle and securing to circumferentially displaced portions of the end tip. The first and second handle portions are axially displaceable relative to each other to enable deflection of the distal end tip in the first and second deflected directions.

According to another aspect of this invention a catheter includes a tubular member with a distal end tip that extends from a proximal end. Steering apparatus selectively deflects the distal end tip in first and second radial directions. The steering apparatus includes proximal support for the tubular member, a slider associated with the proximal support and elements connecting the slider with circumferentially spaced portions of the distal end tip so that axial displacement of the slider in first and second directions correspondingly urge deflection of the distal end tip in first and second radial directions.

According to a further aspect of this invention an improved catheter handle for supporting a catheter with a flexible, distal end tip with steering wires secured to the distal end tip and extending into and secured to the handle. The handle comprises a first housing for supporting the catheter and a second housing slidably engaging and supporting the first housing for relative axial displacement such that axial displacement in a first direction tends to tension one of the steering wires relative to the other steering wire to urge deflection of the distal end tip in a first radial direction and such axial displacement in a second axial direction tends to tension the other steering wire relative to the one steering wire for urging deflection of the distal end tip in a second radial direction.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a plan view of a catheter, partially in cross-section with portions cut-away, constructed in accordance with this invention with a handle at a proximal end and a bidirectional deflectable tip at a distal end;

FIG. 1A is cross-section of the catheter of FIG. 1 taken along section line 1A in FIG. 1;

FIG. 2 is the catheter of FIG. 1 with the distal end tip deflected in a first direction;

FIG. 3 is the catheter of FIG. 1 with the distal end tip deflected in a second direction; and FIG. 4 is an enlarged plan view, partially in cross-section, of a catheter similar to FIG. 1 incorporating another embodiment of the invention.

DESCRIPTION OF ILLUSTRATIVE EMBODIMENTS

As shown in FIG. 1, a bidirectional steerable catheter 10 according to this invention includes a radially flexible, axially stiff tubular body 11 and a slide actuatable handle 12. The tubular body 11 extends proximally along an axis 13 from a distal end tip section 14 with a proximal end 15 of the tubular body 11 being secured in and supported by a first piston member 16 of the handle 12. The first piston member 16 slidably mounts in an aperture of a second piston member 17 to form a first handle portion that, in turn, slidably mounts in an aperture of a handle base 20 as a second handle portion. Control or steering wires 22 and 23 have proximal ends secured in a convenient manner to the handle base 20 and the second piston member 17, respectively. The steering wires 22 and 23, preferably formed of Nitinol, stainless steel or other suitable material, extend distally through the handle 12 and through the tubular body 11.

Distal ends of the steering wires 22 and 23 secure in a known fashion, to circumferentially spaced portions of the distal end tip at positions 24 and 25, respectively. In this embodiment the positions 24 and 25 are diametrically opposed. Axial displacement of the second piston member 17 relative to the handle base section 20 from a neutral position $P_0$ to either position $P_1$ or $P_2$ deflects the distal end tip 14 from its axial orientation in either of two directions, as illustrated in FIGS. 2 and 3, respectively, and as will be further explained hereinafter.

Continuing to refer to FIG. 1 the first piston member 16, the second piston member 17 and the handle base 20 are preferably formed of a relatively hard polymer such as acetal (e.g. Delrin™). The handle base 20 includes set screws 26 and 27 which extend into a central aperture 30 of the handle base 20. The first set screw 26 extends into a axial groove 31 formed in the second piston member 17 so as to limit the axial displacement of the second piston member 17 relative to the handle base member 20. The second set screw 27 extends through a slot 32 formed in the second piston member 17 and thereby limits the proximal axial displacement of the first piston member 16 into the handle base 20. A setscrew 33 secured in the wall of the second piston member 17 extends into a slot 34 in the first piston member 16 to limit thereby the proximal and distal displacement of the first piston member relative to the second piston member 17.

Still referring to FIG. 1, the second piston member 17 further includes a radially extending circumferential bead protuberance 35 proximate a distal end thereof. It is relatively convenient for a surgeon to engage the bead with his or her thumb while holding the handle base 20 in the palm of his or her hand to distally displace and proximally retract the second piston member 17 relative to the handle base 20. Movement of the second piston member 17 proximally in the central cavity 30 of the handle base 20 (i.e., moving the protuberance 35 from the position $P_0$ depicted in FIG. 1 to $P_2$ depicted in FIG. 2) retracts the second piston member 17 into the handle base 20. In addition, as the second piston member 17 retracts, a proximal end 36 of the first piston member 16 abuts the set screw 27 in the handle base 20. As the bead moves from the $P_0$ to the $P_2$ position, the first piston member 16 remains stationary relative to the handle base 20 while the set screw 27, as an urging means, enables the first piston portion 16 to move distally relative to the second piston member 17.

The increase in distance between the proximal end 36 and a proximal end 37 of the second piston member 17 where the steering wire 23 is secured consequently increases the tension or force on the steering wire 23, relative to the force on the steering wire 22. As the tension increases in the steering wire 23 relative to the steering wire 22, the distal end tip 14 deflects from its axial orientation toward the position illustrated in FIG. 2. Moving the bead 35 from the $P_2$ position to the $P_0$ position reduces the tension in the steering wire 23 relative to the steering wire 22 so that the distal end tip 14 tends to return to its axial orientation along the axis 13 as depicted in FIG. 1.

Conversely, as the bead 35 displaces from the $P_0$ position to the $P_1$ position, it engages and urges the first piston 16 distally thereby to increase the tension in the steering wire 22 relative to the tension on the steering wire 23. That is, the distal displacement of the bead 35 from $P_0$ to $P_1$ positions the proximal end 36 of the first piston member 16 distally relative to the handle base 20 without a corresponding changed in position between the first and second piston members 16 and 17. This change in position between the first piston member 16 and the handle base 20 thereby increases the tension in the steering wire 22 relative to the steering wire 23. The distal end tip 14 responds to the increased tension in the steering wire 22 by deflecting the distal tip in the manner depicted in FIG. 3. Thus, a surgeon using the catheter 10 of FIG. 1 can selectively deflect the distal end tip 14 in two directions by selective actuation of the slide actuatable handle 12.

The catheter 10 of FIG. 1 includes electrical contacts 40, 41, 42 and 43 on the distal end tip 14 of the type commonly used in electrophysiological procedures that are disposed. In such an electrophysiology catheter insulated electrical wires (not shown) extend distally through the tubular member 11 and through an aperture in the proximal end 37 of the second piston member 17. The connection of such electrical wires to an electrical source is well known. By way of example, the user could extend through an aperture 45 in a proximal end 46 of the handle base portions 20.

The catheter 10 of FIG. 1 also has indicia 47, 48 and 49 on the outer surface of the second piston member 17. The indicia 47, 48 and 49 are formed as circumferential bands in the surface of the second piston member that correspond with the positioning of the bead 35 at positions $P_0$, $P_1$ and $P_2$, respectively. Thus, a surgeon can easily refer to the indicia 47, 48 and 49 to determine the extent to which the distal end tip is deflected.

In use, a surgeon generally introduces the distal end tip 14 and then the tubular body 11 through an introducer sheath into the vessels of a patient by a known method. The surgeon navigates the distal end tip 14 through the often tortious path by selectively deflecting or steering the distal end tip 14 of the catheter instrument 10 as described above, and by applying torque to the handle 12 of the catheter 10 to rotate the distal end tip 14 to orient the distal end tip 14 in a desired radial orientation.

Once the catheter distal end tip 14 is positioned in a selected portion of the patient's vasculature (e.g. the heart) that is to be, for example, mapped or ablated using the electrodes 40, 41, 42 and 43, the surgeon deflects the distal tip 14 into positions against the desired portions of the heart by appropriate torquing of the handle 12 and displacement of the piston members 16 and 17 relative to the handle base 20.

Unitary transmission of the torque from rotation of the handle 12 is of critical importance in catheters such as the catheter 10. While a wide variety of structures are known, and are suitable for torque transmission in catheters constructed in accordance with this invention, the tubular member 11 of FIG. 1 includes an internal, hollow coil member 50 and braided sheath member 52 overlying the coil 50. Both the members 50 and 52 extend proximally from a proximal base 51 of the distal end tip 14 to the handle 12. A polymeric bio-compatible material 53 overlies the sheath member 50 and the distal end tip 14. Preferably, the structure and materials of the tubular member 11 are substantially the same as that described in the previously referenced U.S. patent application Ser. No. 08/138,863 which is incorporated by reference herein.

FIG. 4 discloses another embodiment of a catheter 110 that includes many of the same features and construction as the catheter 10 of FIG. 1. That is the distal end of the catheter 110 includes the tubular housing 11 that connects with a handle 112. The handle 112 in this instance includes a piston member 117 that supports a proximal end of the tubular member 11 and slides axially along axis 13 within a handle base 120. Screws 122 and 123 secure the proximal end of the steering wires 22 and 23 to the handle base 120. Set screw 126 extends into the central aperture 130 of the handle base 120 with an end of the set screw 126 lying in a slot 131 of the piston member 117 to define thereby the range of motion of the piston member 117 relative to the handle base 120. A bead 135 at the distal end of the piston member 117 provides a convenient member for a surgeon to selectively urge the piston member 117 to and from positions defined as $P_0'$, $P_2'$ and $P_1'$ along axis 13 relative to the handle base 120.

Movement of the piston member 117 relative to the handle base 120 enables a surgeon using the catheter 110 to selectively alter the orientation of the distal end tip 14. The surgeon typically will grasp the handle 112 with the handle base 120 in the palm with a thumb and/or forefinger resting on a bead 135. The surgeon then can, with relative ease, displace the piston member 117 relative to the handle base 120 by applying a force with the adjacent to the bead 135 to move the piston member 117 to the position indicated at $P_1'$ to deflect the distal end tip to the position indicated in phantom at 14A. Likewise the surgeon can retract the bead 135 to the position indicated by $P_2'$ to deflect thereby the distal end tip 14 to the position indicated in phantom 14B.

Thus, both the catheter 110 in FIG. 4 and the catheter 10 of FIG. 1, have the same operating characteristics. However, as can be seen in FIG. 4 the distance from $P_0'$ to $P_2'$ is substantially one half the distance between $P_0'$ and $P_1'$. In this case the proximal end of the steering wire 23 secures to the handle base 20 distally of a proximal end 140 of the piston member 117 so that the proximal end 140 of the piston member 117 acts as a pulley with respect to the steering wire 123. This pulley arrangement provides a two-to-one activation-deactivation ratio with respect to the steering wire 23 compared with the one-to-one activation-deactivation ratio with respect to the steering wire 22. That is, each incremental displacement of the piston member increases/decreases the tension in the steering wire 23 twice as rapidly as the corresponding increase/decrease in tension of the steering wire 22. Thus, the distance from $P_0'$ to $P_2'$ need not be as great as the distance as that from $P_0'$ to P'.

Those skilled in the art will also appreciate that the catheter 110 of FIG. 4 is also depicted as being of the type useful in electrophysiology procedures and would ordinarily include electrical wires (not shown). Thus, like the catheter 10 of FIG. 1, such electrical wires would connect the electrodes 40, 41, 42 and 43 with an electrical source (not shown) and would extend through the tubular member 11 and the handle 120 to a proximal end of the catheter 110.

Thus, in accordance with this invention, a bidirectional steerable catheter with a deflectable distal end tip includes a handle at a proximal end. The handle includes a piston member slidably mounted in a handle base with proximal ends of two steering wires secured in the handle. The steering wires extend through the catheter with respective distal ends thereof secured to circumferentially spaced portions of the distal end tip. Selective axial displacement of the piston member from a neutral position in first and second directions relative to the handle base urges the deflection of the distal end tip in selected first and second radial directions. The piston member can include first and second piston portions with one piston portion slidably mounted inside the other piston portion and the other piston portion being slidably mounted within the handle base. In such case the distal ends of the two steering wires would be secured in the other piston portion and the handle base respectively. Alternatively, the distal ends of the two steering wires can extend through the proximal end of the piston with one wire being secured proximal of the piston member and the other wire being secured distally of the proximal end of the piston member with a segment extending proximally along an outer surface of the piston member.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

We claim:

1. In a bidirectional steerable catheter with a radially flexible, axially extending distal end tip movable from a neutral position to first and second deflected positions, the improvement comprising steering means for enabling selective deflection of the distal end tip to the first and second deflected positions, said steering means comprising first and second steering wires extending through the catheter from a proximal end thereof and being secured at their distal ends to circumferentially displaced positions on the distal end tip and a handle at the proximal end of the catheter with first and second handle portions being axially displaceable relative to each other in first and second axial directions and being attached to said first and second steering wires respectively whereby relative displacement of said handle portions in first and second directions deflects the distal end tip to the first and second deflected portions respectively.

2. A catheter as recited in claim 1 wherein said second handle portion includes an aperture defined therein and wherein said first handle portion mounts in the said aperture to slide with respect to said second handle portion.

3. A catheter as recited in claim 2 wherein one of said first and second handle portions includes visual indicia indicating the corresponding radial displacement of the distal end tip due to the relative axial displacement of said first and second handle portions.

4. A catheter as recited in claim 2 wherein said first handle portion includes an axially extending central aperture through which one of said steering wires extend.

5. A catheter as recited in claim 4 wherein said proximal end of said second steering wire connects to said second handle portion and said first steering wire extends through the axially extending central aperture of said first handle portion and connects to said second handle portion proximally of said proximal end of said second steering wire and proximally of a proximal end of said first handle portion such that the relative displacement of said first and second handle portions in respective axial directions increases and decreases the axial extension of said first steering wire at a rate greater than 1:1.

6. A catheter as recited in claim 5 wherein one of said first and second handle portions includes visual indicia indicating the relative radial displacement of the distal end tip due to the relative axial displacement of said first and second handle portions.

7. A catheter as recited in claim 4 wherein said first housing portion includes a first piston member supporting the proximal end of the catheter and a second piston member supporting said first piston member for axial displacement relative to said second piston member.

8. A catheter as recited in claim 7 wherein said first piston member includes an aperture for enabling extension of the steering wires therethrough, said second piston member includes means for securing said first steering wire thereto and an aperture for enabling extension of said second steering wire therethrough and said second handle portion includes means for securing said second steering wire.

9. A catheter as recited in claim 8 further comprising means, upon proximal displacement of said second piston member from a neutral position relative to said second handle portion, for urging said first piston member distally relative to said second piston member to increase thereby the tension in said first steering wire relative to said second steering wire such that the distal end tip is urged in a first radial deflected orientation and means, upon distal displacement of said second piston member from a neutral relative to said second handle portion, for urging distal displacement of said first piston member relative to said second handle portion to increase thereby the tension in said second steering wire relative to said first steering wire such that the distal end tip is urged in a second radial deflected orientation.

10. A catheter as recited in claim 8 wherein at least one of said first and second piston members include visual indicia indicating the relative radial displacement of the distal end tip due to the relative axial displacement of said first and second handle portions.

11. A catheter as recited in claim 4 wherein said first handle portion includes a first piston member supporting the proximal end of the catheter and a second piston member supporting said first piston member for axial displacement relative to said second piston member being supported by said second handle portion for axial displacement relative thereto.

12. A catheter as recited in claim 1 wherein said first handle portion includes a first piston member supporting the proximal end of the catheter and a second piston member supporting said first piston member for axial displacement relative to said second piston member with said second piston member being supported by said second handle portion for axial displacement relative thereto.

13. A catheter as recited in claim 12 wherein said first and second steering wires are anchored proximally in said handle.

14. A catheter as recited in claim 13 wherein said second steering wire anchors in said second handle portion and said first steering wire anchors in one of said first and second piston members.

15. A catheter as recited in claim 1 wherein said handle further includes a piston member slidably mounted in said first handle portion with said piston member engaging and supporting said catheter extending from said handle portion.

16. A catheter as recited in claim 15 wherein said first handle portion includes an axially extending control aperture through which at least one of said steering wires extends through.

17. A catheter as recited in claim 15 further comprising means upon proximal displacement of said first handle portion from a neutral position relative to said second handle portion for increasing the tension in said first steering wire relative to said second steering such that the distal end tip is urged in a first radial deflected orientation and means, upon distal displacement of said first handle portion from a neutral relative to said second handle portion, for increasing the tension in said second steering wire relative to said first steering wire such that the distal end tip is urged in a second radial deflected orientation.

18. A catheter comprising:
A. an axially, extending, radially flexible, elongated tubular member that extends from a proximal end with an axial stiff portion and with a resilient, radially flexible distal end tip normally extending in an axial direction and defining the distal most portion of said tubular member; and
B. steering means for selectively deflecting said distal end tip in first and second radial directions relative to a neutral position, said steering means including:
   i. support means for supporting said proximal end of said tubular member,
   ii. sliding means associated with said proximal end of said tubular member supported by said support means for selective proximal and distal axial displacement from a neutral position relative to said support means, and
   iii. first and second means for transmitting the relative proximal and distal axial displacement of said sliding means to correspondingly urge the radial displacement of the distal end tip in the first and second directions, respectively, said transmitting means connecting distally to circumferentially spaced portions of said distal end tip and proximally to said sliding means.

19. An improved catheter handle of the type for supporting a catheter distally extending along an axis therefrom, anchoring first and second steering wires extending distally therefrom within the catheter and secured to circumferentially spaced portions of a distal end tip of the catheter, and for selectively deflecting the distal end tip of the catheter from a neutral position in selective first and a second radial direction, the improved catheter handle comprising a first housing for supporting a catheter, a second housing slidably engaging said first housing for axial displacement relative to said first housing, such that relative displacement of said housings in a first axial direction tensions one of the cables and reduces the tension on the other of the cables and relative displacement of said housings in a second opposite axial direction tensions the other of the cables and reduces the tension on the one of the cables such that the relative axial displacement of said housings urge radial deflection of the distal end tip in first and second orientations.

20. A catheter handle as recited in claim 19 wherein said first housing slides within an aperture defined in said second housing and said catheter handle further includes stops limiting the relative axial displacement of said housings between first and second positions.

21. A catheter handle as recited in claim 20 wherein said second housing includes means for mounting the first steering wire proximate a distal end of the second housing and means for mounting the second steering wire proximally of said proximal end of said first steering wire and proximally of a proximal end of said first housing through which said second steering extends.

22. A catheter handle as recited in claim 19 wherein said first housing includes a first piston portion supporting the proximal end of the catheter and a second piston portion supporting said first piston portion for axial displacement relative to said second piston portion with said second piston portion being supported by said second housing for axial displacement relative thereto.

23. A catheter handle as recited in claim 22 wherein said first piston portion includes an aperture for enabling extension of the steering wires therethrough, said second piston portion includes means for securing the first steering wire and an aperture for enabling extension of the second steering wire therethrough and said second housing includes means for securing the second steering wire.

24. A catheter handle as recited in claim 22 wherein said first piston portion includes an aperture for enabling extension of the steering wires therethrough, said second piston portion includes means for securing the first steering wire and an aperture for enabling extension of the second steering wire therethrough and said second housing includes means for securing the second steering wire such that axial displacement of said first piston member relative to said second piston member alters the tension on said second steering member and the axial displacement of said first piston member relative to said second housing alters the tension on said first steering member.

* * * * *